United States Patent [19]

Robinson

[11] 4,298,544
[45] Nov. 3, 1981

[54] MANUFACTURING PROCESS FOR PREPARING DISUBSTITUTED (N-CYANOIMIDO) CARBONATES

[75] Inventor: Graham E. Robinson, Macclesfield, England

[73] Assignee: Imperial Chemical Industries Limited, London, England

[21] Appl. No.: 118,066

[22] Filed: Jan. 24, 1980

[30] Foreign Application Priority Data

Jan. 26, 1979 [GB] United Kingdom ............... 79/02931
Jan. 26, 1979 [GB] United Kingdom ............... 79/02932

[51] Int. Cl.$^3$ ................. C07C 125/08; C07D 319/04; C07D 317/10
[52] U.S. Cl. .................. 260/453 RW; 260/340.7; 260/340.9 R
[58] Field of Search ...... 260/453 RW, 340.7, 340.9 R

[56] References Cited

U.S. PATENT DOCUMENTS 2,708,189  5/1955  Nelb et al. ..................... 260/453.7
2,881,071  4/1959  Buckman et al. ............ 260/453 RW
4,235,802 11/1980  Fuchs .......................... 260/453 RW

FOREIGN PATENT DOCUMENTS 467349  8/1950  Canada ........................ 260/453 RW
14064   8/1980  European Pat. Off. .

OTHER PUBLICATIONS

Huffman et al., J. Org. Chem., 28, pp. 1816-1821 (1963).
Heitke et al., J. Org. Chem., 39, 1522-1526 (1974).
Addor, J. Org. Chem. 29, 738-742 (1964).
Nef, Annalen, 287, 310-325 (1895).
Allenstein et al., *Chem. Ber.* 100 (8), pp. 2604-2615.

*Primary Examiner*—Ethel G. Love
*Attorney, Agent, or Firm*—Cushman, Darby & Cushman

[57] ABSTRACT

A process for the manufacture of disubstituted (N-cyanoimido)carbonate of the formula:

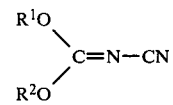

I in which $R^1$ and $R^2$ are the same and are alkyl radicals of 1 to 6 carbon atoms or phenyl radicals, or $R^1$ and $R^2$ are joined to form an ethylene or propylene chain which is optionally substituted by 1 or 2 alkyl radicals each of 1 to 3 carbon atoms, by reaction of a disubstituted imidocarbonate of the formula:

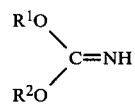

II with cyanamide, characterized in that the reaction is conducted in a two phase system containing water and a water-immiscible organic solvent.

10 Claims, No Drawings

MANUFACTURING PROCESS FOR PREPARING DISUBSTITUTED (N-CYANOIMIDO) CARBONATES

This invention relates to a process for the manufacture of a valuable chemical intermediate.

In German Patent Application P2817078.8 there is described the preparation of histamine H-2 antagonists, which are useful in the treatment of peptic ulcers and other related conditions, using dimethyl and diethyl (N-cyanoimido)-carbonates. Other histamine H-2 antagonists, such as those described in Belgian Pat. No. 866155 and European Patent Publications 0003640, 0006286 and 0006679, as well as those described in, for example, UK Pat. Nos. 1,338,169 and 1,397,436, may be prepared using the same intermediates. The preparation of dimethyl (N-cyanoimido)carbonate from dimethyl (N-cyanoimido)dithiocarbonate is described in J. Org. Chem., 1974, 39, 1522. The preparation of diethyl (N-cyanoimido)-carbonate by reaction of diethyl imidocarbonate with cyanamide in a non-aqueous solvent at 0° C. is described in *Chem Ber.*, 1967, 100, 2604.

It has now been discovered, and herein lies our invention, that these compounds may be prepared, in high yield and in pure form, by reaction of the appropriate imidocarbonate with cyanamide under aqueous conditions.

According to the invention there is provided a process for the manufacture of a disubstituted (N-cyanoimido)carbonate of the formula:

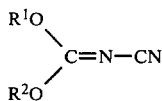   I in which $R^1$ and $R^2$ are the same and are alkyl radicals of 1 to 6 carbon atoms or phenyl radicals, or $R^1$ and $R^2$ are joined to form an ethylene or propylene chain which is optionally substituted by 1 or 2 alkyl radicals each of 1 to 3 carbon atoms, by reaction of a disubstituted imidocarbonate of the formula:

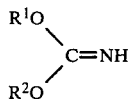   II with cyanamide, characterised in that the reaction is conducted in a two phase system containing water and a water-immiscible organic solvent.

A particular value for $R^1$ or $R^2$ is, for example, a methyl, ethyl or isopropyl radical. When $R^1$ and $R^2$ are joined to form an ethylene or propylene radical, a particular value for the optional alkyl substituent is a methyl radical.

A preferred pH for the reaction is in the range 4 to 10, and a particularly preferred pH is in the range 5 to 8.

A particular water-immiscible organic solvent is, for example, an alkyl or dialkyl benzene in which the alkyl radicals are of 1-6 carbon atoms, for example toluene, xylene or ethylbenzene, or methylene chloride, ethyl acetate, ether, chloroform, chlorobenzene, n-butanol or isobutanol. A preferred water-immiscible organic solvent is toluene.

The process may be conducted at a temperature in the range $-15°$ to $60°$ C., and preferably at a temperature in the range $-5°$ to $25°$ C. A particularly preferred temperature is in the range $5°$ to $25°$ C.

The process may be carried out over a period of from 5 minutes to 24 hours, and preferably over a period of 5 minutes to 1 hour. The cyanamide may be used as the free base or as a salt such as the hydrochloride, hydrobromide, dihydrochloride or dihydrobromide. The dihydrochloride or dihydrobromide may be used in the solid form, as such, or the hydrochloride, hydrobromide, dihydrochloride or dihydrobromide may be used in the form of an aqueous solution. Alternatively, any one of these salts may be prepared in situ in the reaction mixture.

The product may be isolated by separation of the water-immiscible solvent from the aqueous layer, optionally followed by a further extraction of the aqueous layer with a water-immiscible organic solvent. The product may be isolated by evaporation of the organic solvent to dryness, or the product may be precipitated by addition of an organic solvent in which the product has very low solubility, for example petroleum ether or hexane. Such an addition may be made after an optional reduction in the volume of the water-immiscible organic solvent. The precipitation of the product may be encouraged by cooling the solvent mixture, for example to 0° C. The product may, if necessary, be recrystallised from a solvent such as a mixture of methylene chloride and ether, or a mixture of toluene and hexane.

According to a subsidiary feature of the invention, the starting material of the formula II may itself be manufactured in situ by treatment of cyanogen chloride or cyanogen bromide with the appropriate alcohol or diol in a two phase system containing water and a water-immiscible organic solvent. The reaction is preferably conducted in the presence of a base. When $R^1$ and $R^2$ are alkyl or phenyl radicals, the cyanogen chloride or cyanogen bromide is preferably reacted with two or more molecular equivalents of an alcohol of the formula $R^1$-OH in the presence of slightly more than one equivalent of a base. When $R^1$ and $R^2$ are joined, the cyanogen chloride or cyanogen bromide is reacted with one or more molecular equivalents of diol in the presence of slightly more than one equivalent of base. The base used may be in the form of an alkoxide derived from the alcohol or diol employed in the subsidiary process of the invention. When so used, the minimum amount of free alcohol or diol required is reduced by an amount equivalent to the amount of alkoxide used. Alternatively the base may, for example, be an alkali or alkaline earth metal hydroxide such as sodium or potassium hydroxide. A preferred base is sodium hydroxide. The alcohol and/or the base may be used in amounts considerably in excess of the minimum amounts quoted above. Thus, for example, when $R^1$ and $R^2$ are alkyl or phenyl radicals, from 2 to 10, and preferably from 3 to 4, molecular equivalents of alcohol $R^1$-OH may be used, and from $>1.0$ to 5, and preferably 1.1 to 1.5, equivalents of base may be used. When $R^1$ and $R^2$ are joined, the number of molecular equivalents of diol which may be used is from 1 to 5, and preferably from 1.5 to 2. The base is preferably present in such amount that the pH of the reaction medium in the subsidiary process is in the range 11 to 15. The subsidiary process may be conducted at a temperature in the range $-15°$ to $60°$ C., and preferably in the range $-5°$ to $25°$ C. A particularly preferred temperature is in the range $5°$ to $25°$ C. The water-immiscible organic solvent is preferably the same as that used in the main process of the invention. A solvent which is unstable to base, for example ethyl acetate, cannot however be used. If an alcoholic solvent is used, it must be the same alcohol or diol as that which participates in the reaction. The subsidiary process may be conducted over a period of between 5 minutes and 24 hours, and preferably over a period of between 30 minutes and 10 hours.

At the completion of the subsidiary process of the invention, the pH of the reaction mixture may be lowered to the preferred pH range for the main process of the invention by the addition of a strong mineral acid such as hydrochloric or sulphuric acid.

It is considered that the preparation of the compound of the formula II described above is also an inventive process. Thus the preparation of diethyl imidocarbonate from cyanogen chloride by reaction with anhydrous ethanol and sodium ethoxide at −10° C. is described in Annalen, 1895, 287, 310. When water, or a temperature above 0°, was used by-products were formed. The product was also difficult to isolate when water was used. It has now been discovered, and herein lies our invention, that such a product may be obtained in high yield and in pure form by reaction with the cyanogen chloride and the appropriate alcohol or diol under aqueous conditions.

According to the invention there is provided a process for the manufacture of a disubstituted imidocarbonate of the formula:

in which $R^1$ and $R^2$ are the same and are alkyl radicals of 1 to 6 carbon atoms or phenyl radicals, or $R^1$ and $R^2$ are joined to form an ethylene or propylene chain which is optionally substituted by 1 or 2 alkyl radicals each of 1 to 3 carbon atoms, by reaction of cyanogen chloride or cyanogen bromide with the appropriate alcohol or diol, characterised in that the reaction is conducted in a 2 phase system containing water and a water-immiscible organic solvent.

Particular and preferred conditions for this invention are the same as those specified for the preparation of the compound of the formula II in the subsidiary process of the invention given above.

The invention is illustrated, but not limited, by the following Examples in which Example 3 illustrates a preferred process.

EXAMPLE 1

A concentrated aqueous sodium hydroxide solution was prepared by dissolving sodium hydroxide (46 g.) in water (53 ml.). A weighed amount of this solution (58.6 g., containing 27.1 g., 0.677 moles, of sodium hydroxide) was diluted with water (20 ml.) and the diluted solution was added to a mixture of methanol (54.2 g., 1.69 moles) and toluene (90 ml.) with stirring at 0°–5° C. A solution of cyanogen chloride (34.7 g., 0.564 moles) in toluene (25 ml.) was added over 1 hour, the temperature of the reaction mixture being maintained at 0°–5° C., and the mixture was then stirred for a further 2 hours at 0°–5° C. Concentrated hydrochloric acid (61.5 g. of a solution prepared by adding 36 g. of HCl to 64 ml. of water, equivalent to 22.2 g, 0.609 mole, of HCl) was then added, keeping the temperature below 5° C., until the pH of the reaction mixture had fallen to 7 (about 13 ml. of the acid having been added). An aqueous solution of cyanamide (42.3 g. of a solution prepared by dissolving 50 g. of cyanamide in 50 ml. of water, equivalent to 21.2 g, 0.508 mole, of cyanamide) was then added simultaneously with the remainder of the acid. The temperature of the mixture was then raised to 20° C. over 1 hour. Water (40 ml.) was added and when all the sodium chloride had dissolved, the layers were separated. The aqueous layer was extracted with toluene (2×50 ml.) and the combined toluene solutions were washed with saturated aqueous sodium chloride (2×15 ml.) and evaporated to give dimethyl(N-cyanoimido)carbonate (47.1 g., 73.3%) as a white solid. Alternatively, the product was isolated by concentrating the combined toluene solutions to about 30 ml. and adding about 40 ml. of hexane. The product had m.p. 62°–64° C. on recrystallisation from methylene chloride/ether 1:2 v/v. The melting point reported in *J. Org. Chem.*, 1974, 11, 1524, is 52°–56° C.

EXAMPLE 2

Cyanogen chloride (8.67 g.; 0.141 moles) was dissolved in absolute ethanol (33 ml.; 0.57 moles) with stirring. Toluene (37.5 ml.) was added and the solution was cooled in an ice/salt bath to −10° C. A solution of sodium hydroxide (11.24 g.; 0.281 moles) in water (29 ml.) was added over 1 hour, maintaining the temperature at −10° to −5° C. The reaction mixture was then stirred at −5° C. for a further 1 hour. Concentrated hydrochloric acid 36% w/w (23.0 g.≡8.28 g. HCl, 0.227 moles) was added dropwise, maintaining the temperature at −5° C., and when half of the acid had been added a solution of cyanamide (4.74 g.; 0.113 moles) in water (4.7 ml.) was added simultaneously with the remainder of the acid. The total time for the addition was 40 minutes and the final pH was 6–7. The cooling bath was removed and the reaction mixture was allowed to warm to room temperature over 30 minutes. The toluene layer was separated and the aqueous solution was extracted with ethyl acetate (2×50 ml.). The organic solutions were combined, washed with water (3×25 ml.), dried (MgSO$_4$) and evaporated to give diethyl (N-cyanoimido)carbonate (10.19 g.; 51%) as a yellow oil. The infra-red spectrum (liquid film) of the product was identical to that described in *Chem. Ber.* 1967, 100, 2604.

EXAMPLE 3

A mixture of toluene (300 ml.) and methanol (120 g., 3.75 g. moles) was stirred and cooled to 10°–15° C. A solution of sodium hydroxide (45.1 g., 1.13 g. moles) in water (50.9 ml.) was added to the mixture keeping the temperature below 15° C. Cyanogen chloride (58.0 g. 0.94 g. moles) was then passed into the reaction vessel at such a rate as to maintain the temperature in the range 0°–15° C. After this addition the mixture was stirred for 2 hours during which time the temperature was lowered to 31 10° to −5° C. Concentrated hydrochloric acid (19.0 g. of a solution prepared by adding 36 g. of HCl to 64 ml. of water, equivalent to 6.8 g., 0.19 g. mole, of HCl) was then added over about 10 minutes after which the pH of the reaction mixture was 8–9. Without delay a mixture of an aqueous solution of cyanamide (63 g. of a solution prepared by dissolving 50 g. of cyanamide in 50 ml. of water, equivalent to 31.5 g., 0.75 g. mole, of cyanamide) and concentrated hydrochloric acid (72.5 g. of a solution prepared by adding 36 g. of HCl to 64 ml. of water, equivalent to 26.0 g., 0.71 g. mole, of HCl) was added over about 10 minutes keeping the temperature of the reaction mixture below 15° C. The pH of the mixture at the end of the addition was about 6. The mixture was warmed to 20°-25° C. and stirred at that temperature for 1 hour. Water (120 ml) was added to this reaction mixture to dissolve the sodium chloride and the layers were separated. The aqueous solution was extracted with more toluene (2×90 ml.). The three toluene solutions were combined and washed with a solution of sodium chloride (14 g.) in water (41 ml.). The toluene solution was stirred and diluted with cyclohexane (500 ml.) and the mixture was then stirred at −5° to 0° C. for 2 hours. Filtration afforded dimethyl(N-cyanoimido)carbonate (58.1 g., 54%) as a white cyrstalline solid which was washed with cyclohexane (100 ml.) and dried in vacuo at 20° C.

EXAMPLE 4

A concentrated aqueous sodium hydroxide solution was prepared by dissolving sodium hydroxide (46 g.) in water (53 ml.) A weighed amount of this solution (87.7 g., containing 40.8 g., 1.02 g. moles, of sodium hydroxide) was diluted with water (29 ml.) and the diluted solution was added to a mixture of methanol (67.7 g., 2.11 g. moles) and toluene (125 ml). with stirring at 0°-5° C. A solution of cyanogen chloride (32.5 g., 0.53 g. moles) in toluene (25 ml.) was then added maintaining the temperature of the reaction mixture below 5° C. The mixture was stirred at 0°-5° C. for 1 hour then water (50 ml.) was added and stirring was continued at 0°-5° C. for a further 2 hours. Concentrated hydrochloric acid (96.4 g. of a solution prepared by adding 36 g. of HCl to 64 ml. of water, equivalent to 34.7 g., 0.95 g. mole, of HCl) was added over 30 minutes keeping the temperature below 5° C. and then an aqueous solution of cyanamide (b 40.7 g. of a solution prepared by dissolving 50 g. of cyanamide in 50 ml. of water, equivalent to 20.4 g., 0.49 g. mole, of cyanamide) was added over 2 minutes at 2° C. The mixture was stirred at 20°-25° C. for 30 minutes and the layers were separated. The aqueous layer was extracted with toluene (2×50 ml.). The toluene solutions were combined, washed with saturated aqueous sodium chloride solution (2×15 ml.) and evaporated to give dimethyl (N-cyanoimido)carbonate (20.3 g., 33%) as a white solid.

EXAMPLE 5

A concentrated aqueous sodium hydroxide solution was prepared by dissolving sodium hydroxide (46 g.) in water (53 ml.). A weighed amount of this solution (91.3 g. containing 42.4 g., 1.06 g. moles, of sodium hydroxide) was diluted with water (30 ml.) and the diluted solution was added to a mixture of methanol (70.4 g., 2.2 g. moles) and toluene (125 ml.) with stirring at 0°-5° C. A solution of cyanogen chloride (33.8 g., 0.55 g. moles) in toluene (25 ml.) was then added, maintaining the temperature of the reaction mixture below 5° C. The mixture was stirred at 0°-5° C. for 1 hour then water (50 ml.) was added and the mixture was stirred at 0°-5° C. for a further 2 hours. Concentrated hydrochloric acid (53.0 g. of a solution prepared by adding 36 g. of HCl to 64 ml. of water, equivalent to 19.1 g., 0.52 g. mole, of HCl) was added, keeping the temperature at 0°-5° C., to give a pH of 8. An aqueous solution of cyanamide (42.4 g. of a solution prepared by dissolving 50 g. of cyanamide in 50 ml. of water, equivalent to 21.2 g., 0.50 g. mole, of cyanamide) was added quickly and then more concentrated hydrochloric acid (47.2 g. of solution, equivalent to 17.0 g., 0.47 g. mole, of HCl) was added keeping the temperature at 0°-5° C. The mixture was stirred for 30 minutes at 20°-25° C. and the layers were separated. The aqueous layer was extracted with toluene (2×50 ml.). The toluene solutions were combined, washed with saturated aqueous sodium chloride solution (2×15 ml.) and evaporated to give dimethyl(N-cyanoimido)carbonate (27.8 g., 44%) as a white solid.

EXAMPLE 6

A concentrated aqueous sodium hydroxide solution was prepared by dissolving sodium hydroxide (46 g.) in water (53 ml.). A weighed amount of this solution (70.5 g., containing 32.8 g., 0.82 g. mole, of sodium hydroxide) was diluted with water (24 ml.) and the diluted solution was added to a mixture of methanol (54.4 g., 1.70 g. mole) and toluene (125 ml.) with stirring at 0°-5° C. A solution of cyanogen chloride (26.1 g., 0.42 g. mole) in toluene (45 ml.) was added over 30 minutes maintaining the temperature at 0°-5° C. and the mixture was stirred at 0° C. for 90 minutes. Water (50 ml.) was then added, followed by concentrated hydrochloric acid (41.0 g. of a solution prepared by adding 36 g. of HCl to 64 ml. of water, equivalent to 14.8 g., 0.40 g. mole, of HCl) which was added all at once. The temperature rose to 27° C. and the pH was 8. An aqueous solution of cyanamide (32.7 g. of a solution prepared by dissolving 50 g. of cyanamide in 50 ml. of water, equivalent to 16.4 g., 0.39 g. mole, of cyanamide) and more concentrated hydrochloric acid (36.4 g. of solution, equivalent to 13.1 g., 0.36 g. mole, of HCl) were added simultaneously to the mixture over 5 minutes. The temperature of the mixture rose to 38° C. and the final pH was 6. The mixture was stirred for 30 minutes at 20°-25° C. and the layers were separated. The aqueous layer was extracted with toluene (2×50 ml.). The toluene solutions were washed with saturated aqueous sodium chloride solution (2×15 ml.) and evaporated to give dimethyl (N-cyanoimido)carbonate (32.5 g., 67%) as a white solid.

EXAMPLE 7

A concentrated aqueous sodium hydroxide solution was prepared by dissolving sodium hydroxide (46 g.) in water (53 ml.). A weighed amount of this solution (51.5 g., containing 23.9 g., 0.60 g. moles, of sodium hydroxide) was added to a mixture of methanol (56.9 g., 1.78 g. moles) and toluene (150 ml.) over 12 minutes with stirring at 15°-20° C. The mixture was warmed to 40° C. and then a solution of cyanogen chloride (31.0 g., 0.50 g. mole) in toluene (25 ml.) was added over 40 minutes, maintaining the temperature of the mixture at 40°-45° C. The mixture was cooled to 20° C. and concentrated hydrochloric acid (10.3 g. of a solution prepared by adding 36 g. of HCl to 64 ml. of water, equivalent to 3.7 g., 0.10 g. mole, of HCl) was added over 14 minutes maintaining the temperature of the mixture at 15°-20° C.; the pH at the end of the addition was 7-8. A mixture of an aqueous solution of cyanamide (38.2 g. of a solution prepared by dissolving 50 g. of cyanamide in 50 ml. of water, equivalent to 19.1 g., 0.45 g. mole, of cyanamide) and concentrated hydrochloric acid (40.9 g. of solution, equivalent to 14.7 g., 0.40 g. mole, of HCl) was then added over 3 minutes; the pH at the end of this addition was 5-6. Water (60 ml.) was added, the mixture was stirred for 30 minutes at 20–25° C. and then the layers were separated. The aqueous layer was extracted with toluene (2×50 ml.) and the toluene solutions were combined, washed with saturated aqueous sodium chloride solution (25 ml.) and evaporated to give dimethyl (N-cyanoimido)carbonate (29.5 g., 51%) as a white solid.

What we claim is:

1. A process for the manufacture of a disubstituted (N-cyanoimido)carbonate of the formula:

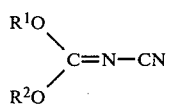   I in which $R^1$ and $R^2$ are the same and are alkyl radicals of 1 to 6 carbon atoms or phenyl radicals, or $R^1$ and $R^2$ are joined to form an ethylene or propylene chain which is optionally substituted by 1 or 2 alkyl radicals each of 1 to 3 carbon atoms, by reaction of a disubstituted imidocarbonate of the formula:

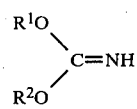   II with cyanamide, characterised in that the reaction is conducted in a two phase system containing water and a water-immiscible organic solvent.

2. A process as claimed in claim 1 in which $R^1$ is a methyl or ethyl radical.

3. A process as claimed in claim 2 in which the pH of the reaction mixture is in the range 5 to 8.

4. A process as claimed in claim 2 in which the temperature of the reaction mixture is in the range 5° to 25° C.

5. A process as claimed in claim 3 or 4 in which the water-immiscible organic solvent is toluene.

6. A process as claimed in claim 1 in which the starting material of the formula II is manufactured in situ by treatment of cyanogen chloride or cyanogen bromide with the appropriate alcohol or diol in a two phase system containing water and a water-immiscible organic solvent.

7. A process as claimed in claim 6 in which, in the preparation of the starting material of the formula II, the reaction is conducted in the presence of a base.

8. A process as claimed in claim 6 in which, in the preparation of the starting material of the formula II, the pH of the reaction mixture is in the range 11 to 15.

9. A process as claimed in claim 6 in which, in the preparation of the starting material of the formula II, the temperature of the reaction mixture is in the range 5° to 25° C.

10. A process for the manufacture of a disubstituted imidocarbonate of the formula:

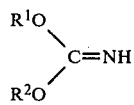   II in which $R^1$ and $R^2$ are the same and are methyl or ethyl, or $R^1$ and $R^2$ are joined to form an ethylene or propylene chain which is optionally substituted by 1 or 2 alkyl radicals each of 1 to 3 carbon atoms, by reaction of cyanogen chloride or cyanogen bromide with the appropriate alcohol or diol, characterised in that the reaction is conducted in a two phase system containing water and a water-immiscible organic solvent.

* * * * *